(12) United States Patent
Hauch

(10) Patent No.: US 10,006,090 B2
(45) Date of Patent: Jun. 26, 2018

(54) METHOD FOR THE QUANTIFICATION, QUALITATIVE GENETIC CHARACTERIZATION AND GENE EXPRESSION CHARACTERIZATION OF PREDETERMINED CELLS

(71) Applicant: ADNAGEN GMBH, Hannover-Langenhagen (DE)

(72) Inventor: Siegfried Hauch, Isernhagen Süd (DE)

(73) Assignee: ADNAGEN GMBH, Langenhagen (DE)

( * ) Notice: Subject to any disclaimer, the term of this patent is extended or adjusted under 35 U.S.C. 154(b) by 0 days. days.

(21) Appl. No.: 14/371,311

(22) PCT Filed: Jan. 8, 2013

(86) PCT No.: PCT/EP2013/050181
§ 371 (c)(1),
(2) Date: Jul. 9, 2014

(87) PCT Pub. No.: WO2013/104599
PCT Pub. Date: Jul. 18, 2013

(65) Prior Publication Data
US 2015/0045246 A1    Feb. 12, 2015

(30) Foreign Application Priority Data
Jan. 12, 2012  (EP) ..................... 12000156

(51) Int. Cl.
*C12Q 1/68* (2018.01)
*C12Q 1/6886* (2018.01)
*C12Q 1/6806* (2018.01)

(52) U.S. Cl.
CPC ......... *C12Q 1/6886* (2013.01); *C12Q 1/6806* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

2007/0031876 A1    2/2007  Lin et al.

FOREIGN PATENT DOCUMENTS

| EP | 2098536 A1 | 9/2009 |
|---|---|---|
| WO | 2003023057 A2 | 3/2003 |

OTHER PUBLICATIONS

Pantel, Klaus et al: "Circulating tumour cells 1-16 in cancer patients: challenges and perspectives", Trends in Molecular Medicine, Elsevier Current Trends, GB, vol. 16, No. 9, Sep. 1, 2010 (Sep. 1, 2010) , pp. 398-406, XP 027433109, ISSN: 1471-4914, DOI: 10.1016/J.MOLMED.2010.07.001 [retrieved on Jul. 29, 2010] p. 400, table 1.

Pachmann, Katharina et al: "Standardized quantification of circulating peripheral tumor cells from lung and breast cancer", Clinical Chemistry and Laboratory Medicine, Walter De Gruyter & Co, Berlin, New York, vol. 43, No. 6, Jan. 1, 2005 (Jan. 1, 2005), pp. 617-627, XP009112550, ISSN: 1434-6621, DOI: 10.1515/CCLM. 2005.107, p. 618, right-hand column.

Liu, Zhian et al: "Negative enrichment by immunomagnetic nanobeads for unbiased characterization of circulating tumor cells from peripheral blood of cancer patients", Journal of Translational Medicine, vol. 9, No. 1, Jan. 1, 2011 (Jan. 1, 2011), pp. 70-70, XP055028555, ISSN: 1479-5876, DOI: 10.1186/1479-5876-9-70 cited in the application p. 2, "Materials and methods".

Alunni-Fabbroni, Marianna et al: "Circulating tumour cells in clinical practice: Methods of detection and possible characterization", Methods: A Companion to Methods in Enzymology, Academic Press Inc., New York, NY, US, vol. 50, No. 4, Apr. 1, 2010 (Apr. 1, 2010), pp. 289-297, XP026966683, ISSN: 1046-2023 [retrieved on Jan. 29, 2010] p. 290, table 1.

International Search Report and Written Opinion of the International Searching Authority for PCT/EP2013/050181, dated Apr. 15, 2013 (Apr. 15, 2013), the whole document.

International Search Report dated Mar. 14, 2017, issued in International Application No. PCT/IB2016/001318.

Written Opinion of the International Searching Authority dated Mar. 14, 2017, issued in International Application No. PCT/IB2016/001318.

(Continued)

*Primary Examiner* — Nancy A Treptow
(74) *Attorney, Agent, or Firm* — Rankin, Hill & Clark LLP

(57) ABSTRACT

In the present invention, a method for the qualitative genetic characterization and/or gene expression characterization of predetermined cells in a fluid sample containing such cells is provided. The inventive method for the qualitative genetic and/or gene expression characterization of predetermined cells in a fluid sample containing such cells, comprises: a) selectively extracting at least a part of the predetermined cells from the sample forming a cell suspension $cs_0$; and b) repeating the extraction step a) n times with the same sample of step a), with n≥1, forming at least one cell suspension $cs_n$; c) determining a gene expression profile $gep_n$ and/or a first copy number count $cnc_0$ of at least one DNA and/or RNA with at least a part of the cell suspension $cs_0$; d) determining at least one further gene expression profile gepn and/or a further copy number count $cnc_n$ of at least one DNA and/or RNA with at least a part of at least one further cell suspension csn; e) calculating the predetermined cells' gene expression profile gep(P) of at least one predetermined DNA and/or RNA by subtracting gepn from gep, and/or the predetermined cells' copy number count cnc(P) of at least one predetermined DNA and/or RNA by subtracting cncn from $cnc_0$; and f) evaluating the qualitative genetic and/or gene expression characteristics of the predetermined cells from gep(P) and/or cnc(P).

18 Claims, 1 Drawing Sheet

(56) References Cited

OTHER PUBLICATIONS

J. Chen et al: "High-throughput platform for real-time monitoring of biological processes by multi color single-molecule fluorescence", Proceedings of the National Academy of Sciences, vol. 111, No. 2, Dec. 30, 2013 (Dec. 30, 2013), pp. 664-669, XP055332961, US ISSN: 0027-8424, DOI: 10.1073/pnas.1315735111 figure 1B.

John Eid et al.: "Real-Time DNA Sequencing fromSingle Polymerase Molecules", Science, vol. 23. No. 5910, Nov. 20, 2008 (Nov. 20, 2008), pp. 133-138, XP055096175, ISSN: 0036-8075. DOI: 10.1126/science.1162986 figure 1.

Sobhy M A et al: "Versatile single-molecule multi-color excitation and detection fluorescence setup for studying biomolecular dynamics", Review of Scientific Instruments, AIP, Melville, NY, US, vol. 82, No. 11, Nov. 1, 2011 (Nov. 1, 2011), pp. 113702-113702, XP012152143, ISSN: 0034-6748, DOI: 10.1063/1.3657153 [retrieved on Nov. 7, 2011] p. 113706, col. 2; figures 3, 5,6.

Van Guo et al: "CMOS Time-Resolved. Contact, and Multispectral Fluorescence Imaging for DNA Molecular Diagnostics", Sensors, vol. 14. No. 11, Oct. 31, 2014 (Oct. 31, 2014), pp. 20602-20619, XP055333528, DOI: 10.3390/s141120602.

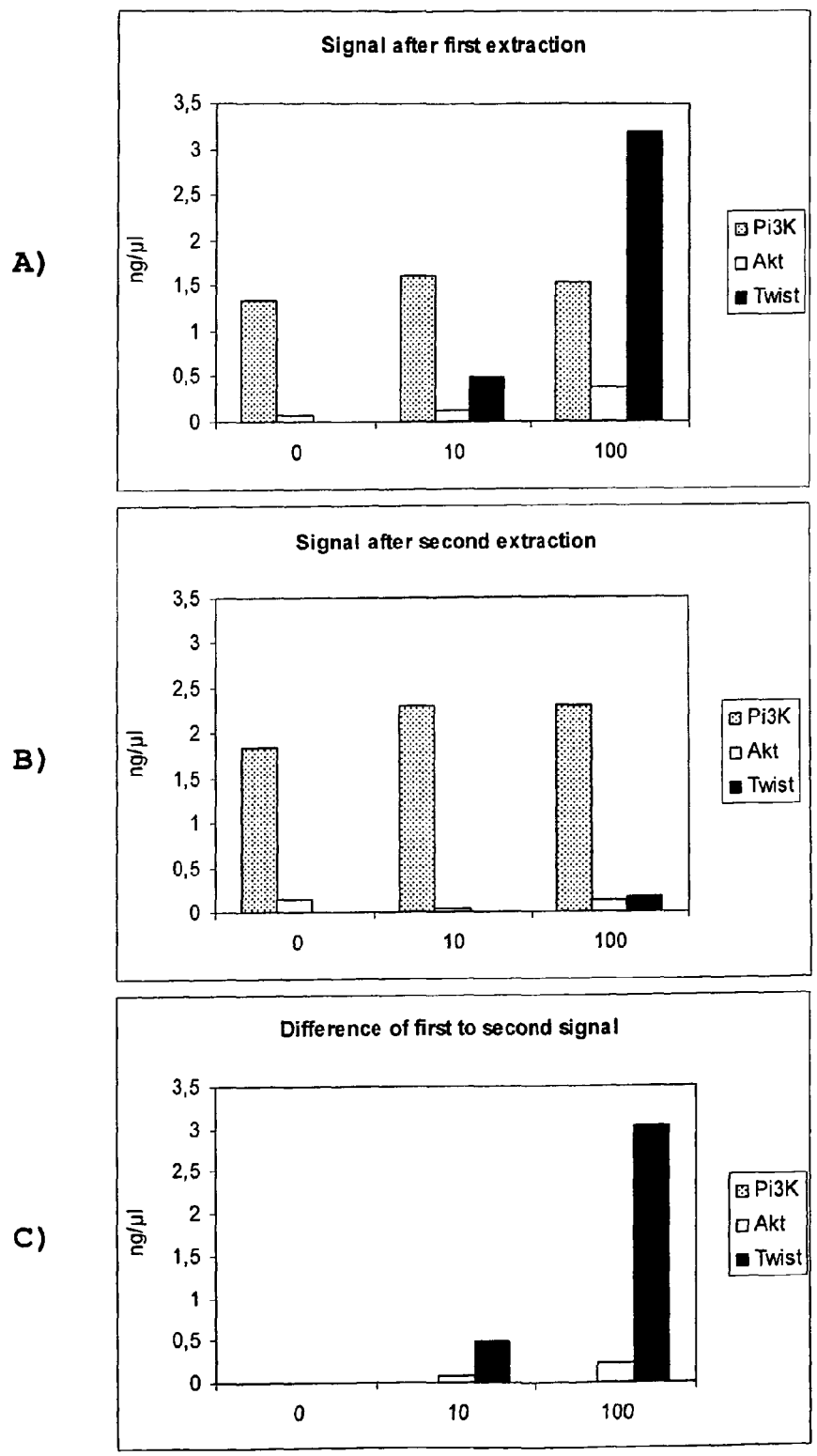

METHOD FOR THE QUANTIFICATION, QUALITATIVE GENETIC CHARACTERIZATION AND GENE EXPRESSION CHARACTERIZATION OF PREDETERMINED CELLS

CLAIM FOR PRIORITY

This application claims priority under 35 USC 371 to International Application No. PCT/EP2013/050181, filed on Jan. 8, 2013, which claims priority to European Patent Application No. 12000156.5, which was filed on Jan. 12, 2012, each of which is hereby incorporated by reference in its entirety.

In the present invention, a method for the qualitative genetic characterization and/or gene expression characterization of predetermined cells in a fluid sample containing such cells is provided. According to the invention, a parameter determined for a mixture of predetermined cells and other cells can be corrected in that only the contribution of predetermined cells to the parameter is obtained. The present invention thus enables the selective determination of gene expression profiles and/or copy number of DNA and RNA in predetermined with high accuracy even though said predetermined cells are present in a mixture with other cells. Furthermore, the present invention provides a method for the selective quantification of predetermined cells in a mixture of predetermined cells and other cells.

Using immunobeads or comparable cell enrichment techniques for the enrichment of rare cells (e.g. circulating tumor cells=CTC) in body fluids such as blood samples, one observes frequently a number of at least 1000-10000 contaminating nucleated non-target cells present in the enriched sample.

The molecular profiling of rare cells in blood (e.g. CTC) is limited due to the presence of contaminating leukocytes. The leukocyte background expression level can be estimated using healthy donor samples. However, leukocytes, even those of healthy volunteers, may always differ in their molecular composition and in their activation and/or expression state. Specifically, the intracellular level or copy number of certain RNAs in leukocytes (their transcriptome) is different not only between healthy and sick people but among healthy people as well.

This difference is getting even more important if healthy donor samples are used as a reference to samples obtained from patients that suffer from a disease like cancer since cancer may cause the presence of activated leukocytes and a leukocyte composition that heavily differs in leukocytes from healthy people. In consequence, for a correct assessment of the amount or the transcriptome of certain predetermined cells, the signal obtained must be corrected by subtraction of an ideal reference.

It was discovered in experiments with predetermined cells that are rarely present in body fluids, such as CTC, that selective extraction of said cells with immunobeads comprising antibodies against said cells is only effective up to a certain degree of purity. It was observed that the selectively extracted samples finally still contained about 1000 other cells (e.g. leukocytes or other nucleated cells) as a cross-contamination. Repeated experiments indicated that the contaminating cells cannot be eliminated any more below this limit. It is assumed that unspecific binding of the contaminating cells (e.g. leukocytes) to the immunobeads is responsible for this effect i.e. the binding of contaminating cells is not caused by specific, but unspecific physical interactions with the immunobeads which occur during every extraction step and cannot be prevented. More washing steps reduced unspecific binding, but reduced specific binding as well leading to a loss of sensitivity.

In view of the problem of cross-contamination as an inherent problem of the purification procedure, the number of tumor-associated markers is very limited. The reason is that the signal of the background is so high that the tumor-associated marker must be strongly overexpressed in the predetermined cells (e.g. CTC) in comparison to the contaminating cells (e.g. leukocytes). For example, a ratio of 1 predetermined cell (e.g. CTC) to 1000-10000 contaminating cells (e.g. leukocytes) would require an at least 1000-fold to 10000-fold overexpression of the tumor-associated marker in the predetermined cells compared to the contaminating cells for a reliable diagnosis. Usually, this disadvantageous ratio of predetermined cells to contaminating cells poses significant detection restrictions in terms of the signal-to-noise ratio. As a consequence, the choice of genes and gene expression profiling methods is severely limited (see also O'Hara et al., Clin. Chem. (2004) 50:5).

Thus, for most genes being potential markers for diseases, an accurate gene expression analysis is hardly possible if said gene is expressed in both the predetermined cells and the contaminating cells. In the prior art, the gene expression analysis of predetermined cells in cell mixtures is thus afflicted with a certain error which derives from a signal of the cells which are not the predetermined cells (=the background or reference).

Regarding the contamination of CTC with leukocytes, some groups have tried to improve the signal-to-noise ratio by a so-called negative enrichment strategy (Liu et al., J. Transl. Med. (2011), 9:70). Said strategy aims at reducing the contamination of leukocytes in a sample of CTC and leukocytes (ratio about $1:10^3-10^4$) by depleting leukocytes with magnetic beads coupled to an anti-$CD45^+$ antibody. The strategy suffers the disadvantage that predetermined cells also binding to the $CD45^+$ antibody are depleted as well and thus no true signal of the predetermined cells is obtained.

The problem underlying the invention is the provision of the true signal (e.g. the true cellular mRNA level and/or copy number count of the DNA) of predetermined cells in a sample of predetermined cells and other (contaminating) cells. In other words, the present invention seeks the elimination of variations in the results which are inherent to the methods of the prior art.

The problem of the prior art is solved by the method for the qualitative genetic and/or gene expression characterization of predetermined cells according to claim 1, the method for the quantification of predetermined cells according to claim 5, the method for designing a cancer therapy according to claim 14 and the method for prognosing cancer according to claim 15.

In a first aspect of the invention, a method is provided for the qualitative genetic and/or gene expression characterization of predetermined cells in a fluid sample containing such cells, comprising a) selectively extracting at least a part of the predetermined cells from the sample forming a cell suspension $cs_0$; and b) repeating the extraction step a) n times with the same sample of step a), with n≥1, forming at least one cell suspension $cs_n$;

c) determining a gene expression profile $gep_0$ and/or a first copy number count $cnc_0$ of at least one DNA and/or RNA with at least a part of the cell suspension $cs_0$;

d) determining at least one further gene expression profile $gep_n$ and/or a further copy number count $cnc_n$ of at least one DNA and/or RNA with at least a part of at least one further cell suspension $cs_n$;

e) calculating the predetermined cells' gene expression profile gep(P) of at least one predetermined DNA and/or RNA by subtracting $gep_n$ from $gep_0$ and/or the predetermined cells' copy number count cnc(P) of at least one predetermined DNA and/or RNA by subtracting $cnc_n$ from $cnc_0$; and f) evaluating the qualitative genetic and/or gene expression characteristics of the predetermined cells from gep(P) and/or cnc(P).

In the first aspect of the invention, the at least one RNA can be selected from the group consisting of mRNA, ncRNA, rRNA, tRNA, snRNA, snoRNA, miRNA, dsRNA and viral RNA. Moreover, the at least one DNA can be selected from the group consisting of cellular DNA, viral DNA and bacterial DNA. In this regard, cellular DNA is any DNA which naturally occurs within biological cells. Thus, the term "cellular DNA" comprises DNA of organisms of all three kingdoms of live i.e. eukaryotic cells, bacterial cells and/or archaeal cells.

Regarding the first aspect of the invention, the gene expression profile and/or the first copy number count of at least one DNA and/or RNA can be determined by RT-PCR, qRT-PCR and/or by microchip technology.

According to one preferred embodiment of the first aspect of the invention, the qualitative genetic and/or gene expression characterization comprises or consists of a characterization of genes involved in metabolism.

To evaluate certain genes in the qualitative genetic and/or gene expression characterization according to the first aspect of the invention, certain molecular markers which are specific for said genes may be used. Preferably, the molecular markers are selected from the group consisting of Pi3K, Akt, Twist and ALDH.

In a second aspect of the invention, a method for the quantification of predetermined cells in a fluid sample containing such cells is provided, the method comprising the steps of a) selectively extracting at least a part of the predetermined cells from the sample forming a cell suspension $cs_0$; and b) repeating the extraction step a) n times with the same sample of step a), with n≥1, forming at least one cell suspension $cs_n$;

c) determining a first copy number count $cnc_0$ of at least one DNA and/or at least one predetermined gene with at least a part of the cell suspension $cs_0$;

d) determining at least one further copy number count $cnc_n$ of at least one DNA and/or at least one predetermined gene with at least a part of at least one further cell suspension $cs_n$;

e) calculating the copy number count of the predetermined cells' DNA and/or the predetermined cells' at least one predetermined gene by subtracting $cnc_n$ from $cnc_0$; and f) correlating the resulting copy number count with the number of predetermined cells being present in the fluid sample.

The two methods according to the first and second aspect of the invention represent equal solutions to the particular technical problem of providing the true signal of predetermined cells in a sample of predetermined cells and other (contaminating) cells. By carrying out equivalent method steps, the methods according to the first and second aspect of the invention both eliminate variations in the results which are inherent to the methods of the prior art. Thus, the first and second aspect of the invention are unified by a general inventive concept.

Both aspects of the present invention use to an advantage that the unspecific contamination of contaminating cells in a sample is random and that the contaminating cells are in excess over the predetermined cells. This ensures that the contamination will appear again and again in a second, third and up to n-fold extraction of the sample. Using this strategy in repeated enrichments using the same specimen, a sample is generated which comprises the contaminating cells but lacks the predetermined cells. The result of the calculated difference between the first extraction step of the sample and the sample which lacks the predetermined cells represents the result of pure predetermined cells.

The first and second aspect of the invention have several advantages over the prior art. Firstly, the methods allow the subtraction of an ideal reference i.e. a reference from the same person on the same day. The reference has basically the same composition as the sample probe except that the predetermined cells are lacking (they have been extracted). This results in a high accuracy of the result and values that are closer to the true values i.e. the values of the predetermined cells only.

Secondly, the two aspects of the invention each can be carried out on a short time scale which decreases the danger of changes in the sample quality or even sample destruction. Since possible changes in the original sample affect the sample and the reference equally (except in the content of predetermined cells they are identical), the risk of false high or false low values is minimized.

Thirdly, inter-personal and inter-sample variation is completely ruled out since both the sample and the background (reference) are actually obtained from one sample, one person and also within a short period of time. A preferred embodiment of the first and second aspect of the invention even requires that in each sample extraction after the first sample extraction, the same solid phase (e.g. immunobeads) like in the first extraction is used (of course after eluting the bound cells before each novel use). Thus, errors which are based on inter- and/or intra-batch variations of a solid phase (e.g. immunobeads) are minimized.

According to the second aspect of the invention, the copy number count of at least one DNA and/or at least one predetermined gene may be determined by qPCR and/or by microchip technology.

In the first and/or second aspect of the invention, the extraction in step b) may be repeated 1-10 times, preferably 1-6 times, most preferably 1-2 times.

Furthermore, in the first and/or second aspect of the invention, selective extraction of at least a part of the predetermined cells of the sample is preferably performed by using identical extraction reagents in step a) and b).

In a preferred embodiment of the first and/or second aspect of the invention, step a) is effected by contacting the sample at least one time with a solid phase that preferentially binds the predetermined cells. Subsequently, unbound cells can be removed from the solid phase, preferably by washing the solid phase with at least one buffer. Finally, cells bound to the solid phase can be eluted from the solid phase, preferably by washing the solid phase with at least one further buffer. The skilled person knows which buffers may be used for washing and/or eluting predetermined cells from a solid phase.

The solid phase in the first and/or second aspect of the invention is preferably selected from the group consisting of polymers, plastics, ceramics, glasses, metals, sepharose, agarose and latex. Most preferably, the solid phase comprises or consists of magnetic beads. The solid phase can comprise antibodies and/or antibody derivatives which are preferably immobilized on the surface.

In a further preferred embodiment of the first and/or second aspect of the invention, the fluid sample comprises or consists of peripheral blood, bone marrow, urine, ascites and sputum from a patient. Optionally, the fluid sample comprises or consists of a tissue sample of an organism.

Furthermore, in a preferred embodiment of the first and/or second inventive aspect, the predetermined cells are selected from the group consisting of tumor stem cells and tumor cells in epithelial-mesenchymal transition, preferably circulating tumor cells (CTC).

The invention further provides a method for designing a cancer therapy, comprising performing the method according to the first aspect of the invention, wherein the predetermined cells are CTC and tailoring of the cancer therapy is based on the evaluation in the last step of the method of the first aspect of the invention.

Finally, the invention provides a method for prognosing cancer, comprising performing the method according to the second aspect of the invention, wherein the predetermined cells are CTC and providing a prognosis for cancer based on the number of CTC which is determined in the last step of the method according to the second aspect of the invention.

In a preferred embodiment of the method for prognosing cancer, the method according to the second aspect of the invention carried out for a first time and at least one further subsequent time. A good prognosis is provided if the number of CTC is lower for at least one further subsequent time than for the first time. A bad prognosis is provided if the number of CTC is higher for at least one further subsequent time than for the first time.

According to a most preferred embodiment of the first and/or second aspect of the invention, all steps of the method of the first and/or second aspect of the invention are carried out in vitro.

With reference to the following figures and examples, the subject according to the invention is intended to be explained in more detail without restricting said subject to the special embodiments shown here.

FIG. 1 shows marker signals after the first extraction and second extraction of a sample comprising 0, 10 or 100 IGROV1 tumor cells as well as the calculated gene expression profile of the IGROV1 tumor cells.

FIG. 1 (A) shows is the tumor marker signal (=copy number counts=cnc) of Pi3K, Akt and Twist determined with three different cell suspensions $cs_0$ which were obtained by a first extraction of IGROV1 cells from three blood samples of healthy donors. The first sample did not contain any IGROV1 cells ("0"), the second sample was spiked with 10 IGROV1 cells ("10") and the third sample was spiked with 100 IGROV1 cells ("100"). (B) The tumor marker signal (=cnc) of Pi3K, Akt and Twist determined for three different cell suspensions $cs_1$ which were obtained by a second extraction of IGROV1 cells from the same blood samples as for the first extraction. (C) The tumor marker signals of Pi3K, Akt and Twist which belong only to IGROV1 cells (=cnc(P)) were calculated by subtracting each $gep_1$ from each $gep_0$ for the "0", "10" and "100" sample, respectively.

EXAMPLE 1: Qualitative Gene Expression Characterization of CTC in a Sample Containing CTC and Leukocytes The AdnaTests use an immunobead based technique to enrich circulating tumor cells (CTC) from the blood of cancer patients followed by a molecular determination characterization of such cells using tumor-associated marker gene expression profiles. However, even if the enrichment is quite effective the samples contain finally about 1000 leukocytes or other nucleated cells as a cross contamination.

According to one embodiment of the invention, all CTC plus about 1000 contaminating leukocytes are analyzed in a first enrichment step. Using the same blood sample after this first enrichment step and again extract it with the same immunobeads, the same amount and composition of contaminating leukocytes is captured, but no tumor cells any more. So the second enrichment is the perfect blank sample and can be subtracted from the first sample to mathematically get access to an expression profile that can only be dedicated to the CTC, if there are any.

EXAMPLE 2: Quantitative Determination of IGROV1 Cells in a Blood Sample

In a further example of the invention, the predetermined cells were IGROV1 tumor cells and the fluid sample was a 5 ml blood sample of a healthy person. Firstly, three separate samples of 5 ml blood were spiked with 0, 10 or 100 IGROV1 tumor cells. Then, at least a part of the IGROV1 tumor cells were selectively extracted from the sample forming three different cell suspensions $cs_0$. Secondly, the extraction step was repeated for each of the three samples one further time forming three further cell suspensions $cs_1$. Thirdly, the three copy number counts of the first extraction ($cnc_0$ of "0", "10" and "100") and the three copy number counts of the second extraction ($cnc_1$ of "0", "10" and "100") of the cellular markers Pi3K, Akt and Twist were determined by qRT-PCR (see FIGS. 1A and 1B). Finally, the copy number count cnc(P) of Pi3K, Akt and Twist was calculated by mathematically subtracting each $cnc_1$ from its respective $cnc_0$ (see FIG. 1C).

The invention claimed is:

1. Method for qualitative genetic and/or gene expression characterization of predetermined cells in a fluid sample containing such cells, comprising:
   a) selectively extracting at least a part of the predetermined cells from the sample thereby obtaining an extracted cell suspension $cs_0$, and a sample remainder comprising cells that remain after selective extraction; and
   b) selectively extracting at least a further part of the predetermined cells from the remainder sample thereby obtaining at least one cell suspension $cs_n$, where n represents a number of times selective extraction is repeated and n is ≥1;
   c) determining a gene expression profile $gep_0$ and/or a first copy number count $cnc_0$ of at least one DNA and/or RNA with at least a part of the cell suspension $cs_0$;
   d) determining at least one further gene expression profile $gep_n$ and/or a further copy number count $cnc_n$ of at least one DNA and/or RNA with at least a part of the at least one cell suspension $cs_n$;
   e) calculating the predetermined cells' gene expression profile gep(P) of at least one predetermined DNA and/or RNA by subtracting $gep_n$ from $gep_0$ and/or the predetermined cells' copy number count cnc(P) of at least one predetermined DNA and/or RNA by subtracting $cnc_n$ from $cnc_0$; and
   f) evaluating the qualitative genetic and/or gene expression characteristics of the predetermined cells from gep(P) and/or cnc(P) by applying a specific molecular marker and detecting a marker signal.

2. Method according to claim 1, wherein the at least one RNA is selected from the group consisting of mRNA, ncRNA, rRNA, tRNA, snRNA, snoRNA, miRNA, dsRNA and viral RNA and/or the at least one DNA is selected from the group consisting of cellular DNA, viral DNA and bacterial DNA.

3. Method according to claim 1, wherein the gene expression profile and/or the first copy number count of at least one DNA and/or RNA is determined by RT-PCR, qRT-PCR and/or by microchip technology.

4. Method according to claim 1, wherein the qualitative genetic and/or gene expression characterization comprises or consists of a characterization of genes involved in metabolism.

5. Method according to claim 1, wherein n is $\geq 1$ and $\leq 10$.

6. Method according to claim 1, wherein selective extraction is performed using identical extraction reagents in step a) and in step b).

7. Method according to claim 1, wherein step a) is effected by contacting the sample at least one time with a solid phase that preferentially binds the predetermined cells, subsequently removing unbound cells from the solid phase, and subsequently removing bound cells from the solid phase.

8. Method according to claim 7, wherein the solid phase is selected from the group consisting of polymers, plastics, ceramics, glasses, metals, sepharose, agarose and latex.

9. Method according to claim 7, wherein the solid phase comprises antibodies and/or antibody derivatives.

10. Method according to claim 1, wherein the fluid sample comprises at least one selected from the group consisting of peripheral blood, bone marrow, urine, ascites and sputum obtained from a patient.

11. Method according to claim 1, wherein the predetermined cells are selected from the group consisting of tumor stem cells and tumor cells in epithelial-mesenchymal transition.

12. Method for designing a cancer therapy, comprising:
    i) performing the method according to claim 1, wherein the predetermined cells are circulating tumor cells (CTC); and
    ii) tailoring of the cancer therapy based on the evaluation.

13. Method according to claim 1, wherein n is $\geq 1$ and $\leq 6$.

14. Method according to claim 1, wherein n is 1 or 2.

15. Method according to claim 1, wherein removing unbound cells from the solid phase is by washing the solid phase with at least one buffer and subsequently removing bound cells from the solid phase is by washing the solid phase with at least one further buffer.

16. Method according to claim 7, wherein the solid phase is magnetic beads.

17. Method according to claim 9, wherein the antibodies and/or antibody derivatives are immobilized on a surface of the solid phase.

18. Method according to claim 1, wherein the predetermined cells are circulating tumor cells (CTC).

\* \* \* \* \*